United States Patent [19]
Kusuhara

[11] Patent Number: 5,360,444
[45] Date of Patent: Nov. 1, 1994

[54] OCCLUDER SUPPORTER AND A METHOD OF ATTACHMENT THEREOF

[76] Inventor: Kenji Kusuhara, 4, Ogawa-cho, Nara-shi, Nara-ken, Japan

[21] Appl. No.: 164,880

[22] Filed: Dec. 9, 1993

Related U.S. Application Data

[63] Continuation of Ser. No. 852,650, Mar. 17, 1992, abandoned.

[30] Foreign Application Priority Data

Mar. 19, 1991 [JP] Japan .................... 3-130847

[51] Int. Cl.⁵ .................... A61F 2/24; A61F 2/02; A61F 2/54; A61F 2/76
[52] U.S. Cl. .................... 623/2; 623/11; 623/900; 623/66
[58] Field of Search .................... 623/2, 900, 66, 11, 623/3, 1

[56] References Cited

U.S. PATENT DOCUMENTS

| Re. 30,507 | 2/1981 | Kaster | 623/2 |
| 3,491,376 | 1/1970 | Shiley | 623/2 |
| 3,689,942 | 9/1972 | Rapp | 623/2 |
| 4,343,049 | 8/1982 | Fettel et al. | 623/2 |
| 4,755,181 | 7/1988 | Igoe | 623/2 |
| 4,820,299 | 4/1989 | Philippe et al. | 623/2 |
| 4,822,355 | 4/1989 | Bhuvaneshwar | 623/2 |
| 4,908,028 | 3/1990 | Colon et al. | 623/2 |
| 5,123,918 | 6/1992 | Perrier et al. | 623/2 |

FOREIGN PATENT DOCUMENTS

| 0257874 | 3/1988 | European Pat. Off. | 623/2 |
| 1293014 | 10/1972 | United Kingdom | 623/2 |
| 1466737 | 3/1989 | U.S.S.R. | 623/2 |

*Primary Examiner*—Randall L. Green
*Assistant Examiner*—Dinh X. Nguyen
*Attorney, Agent, or Firm*—Biebel & French

[57] ABSTRACT

The occluder supporter of the present invention is installed to the valve of a mammalian heart and is a device for preventing valve reflux. The characterizing feature of the present invention is the provision of a plurality of stitched attachments which are sewn on to the edge of the occluder and of a support which supports and maintains the edges of the occluder in a mutually close position and which is provided between the stitched attachments in such a way as to transect the valve aperture.

13 Claims, 4 Drawing Sheets

OCCLUDER SUPPORTER AND A METHOD OF ATTACHMENT THEREOF

This is a continuation of co-pending application Ser. No. 07/852,650, filed Mar. 17, 1992, abandoned.

BACKGROUND OF THE INVENTION

1. Technical Field

The present invention relates to a heart occluder supporter, and, in particular, to an occluder supporter which, through its provision to the valves of a mammalian heart, prevents blood from refluxing back through the valve.

2. Related Art

There are four valves present in the mammalian heart. They are the tricuspid valve, the mitral valve, the pulmonary valve, and the aortic valve.

The tricuspid valve is the valve located in the space between the right atrium and the right ventricle. The mitrial valve is the valve located in the space between the left atrium and the left ventricle. The pulmonary valve is the valve located in the space between the right ventricle and the pulmonary artery. The aortic valve is the valve located in the space between the left ventricle and the aorta. Of these, the tricuspid valve and the mitrial valve are called the ventricular valves.

An example of the mitrial valve and the aortic valve and an explanation of their function follows.

First, the case where the function of the mitrial valve is normal will be considered. During the contractions phase of the left ventricle, the mitrial valve is completely shut and the blood within the left ventricle is pumped to the aortic artery. During the relaxation phase of the left ventricle, the mitrial valve is completely open and blood flows into the left ventricle from the left atrium. If, for some reason, a situation occurs wherein the occluder of the bicuspid enlarges, or the chordae tendineae become extended or torn, the mitrial valve is unable to close completely, thereby resulting in a condition where a section of the valve aperture of the mitrial valve remains open. As a result, the opening and closing action of the mitrial valve is imperfect, and a phenomena wherein blood refluxes from the left ventricle into the left atrium (hereafter stated as valve reflux) occurs.

Next, the case where the function of the aortic valve is normal will be considered. During the contraction phase of the left ventricle, the aortic valve is completely open and the blood within the left ventricle is pumped to the aortic artery. During the relaxation phase of the left ventricle, the aortic valve is completely shut and blood flows into the left ventricle from the left atrium. As in the case given above for the mitral valve, if for some reason, a situation occurs wherein the occluder of the aortic valve enlarges, or the valve tip atrophies, the aortic valve is unable to close completely, thereby resulting in a condition wherein a section of the valve aperture of the aortic valve remains open. As a result, the opening and closing action of the valve is imperfect, and a phenomena wherein blood refluxes from the aortic artery to the left ventricle (hereafter stated as valve reflux) occurs.

Valval transplant, valval suturing, and valvoplasty, are among the conventional methods of treatment to correct valve reflux.

Valval transplant is the method of excising the chordae tendineae of the valve tip and attaching an artificial valve or a donor valve to the remaining occluder. Valval suturing is the method of preserving the actual valve itself through suturing the occluder by sewing together one end of the occluder, or through setting the occluder by sewing on a ring to the occluder.

A variety of defects, however, are present in these methods.

For example, in valve substitution, the artificial or donor valve used is considerably expensive and has a short lifetime. Furthermore, in valve suturing and valvoplasty it is not possible to easily prevent valve reflux from occurring through the middle portion of the valve.

SUMMARY OF THE INVENTION

Accordingly, it is an object of the present invention to provide an occluder supporter which solves the problems encountered in the conventional technology and which can effectively prevent the occurrence of valve reflux.

In order to resolve the above problems, an occluder supporter is presented which can, by its installation in a mammalian heart valve, effectively prevent the occurrence of valve reflux. This occluder supporter has a plurality of stitched attachments which are attached to the edge of the occluder, and a support which supports the edges of the stitched attachments so that they are in a mutually close position and which is provided in the space between these stitched attachments so as to transect the valve aperture.

In this occluder supporter, the support holds the edges of the occluder in mutually close position while still providing a center space between them. As a result, even in the case where the occluder has enlarged, the valve can still shut completely and valve reflux can be prevented.

A device having a pair of stitched attachments, attached to the contralateral edges of the occluder, and a support, which holds and supports the contralateral edges in a mutually close position and is provided between the stitched attachments so as to transect the valve aperture, is preferable as an occluder supporter for provision to the ventricle side of the ventricle valve of the heart. Furthermore, it is preferable for the support to bend in such a way that it protrudes out on the ventricle side.

In an occluder supporter, the support holds and supports the contralateral edges of the occluder in a mutually close position while still providing for a center space between the contralateral edges. As a result, even in the event that the occluder has become enlarged or the chordae tendineae have become extended or torn, the aortic valve can still close completely during the contraction of the ventricle, preventing valve reflux. Furthermore, because the support bends in such a way as to protrude out on the atrium side, this support does not come in contact with the valve tip.

A supporter having three stitched attachments attached to each connecting part of the occluder and having a support which holds and supports these connecting part in a mutually close position and which is provided between the stitched attachments in such a way as to transect the valve aperture is preferable as an occluder supporter for provision to the aortic side of the aortic valve of the heart.

In this occluder supporter, the support holds and supports each connecting part of the occluder in a mutually close position, while still providing a center space between them. As a result, even in the event that the occluder has become enlarged or the valve tip has atrophied, the aortic valve can still close completely during the relaxation of the ventricle, preventing valve reflux.

Additionally, a method of attachment of the occluder supporter is proposed herein.

In this method of attachment of the occluder supporter, the support is disposed so as to create a condition wherein the edges of the occluder of a mammalian heart valve are held in a mutually close position, and so as to transect the valve aperture, and to these edges are attached stitched attachments. As a result, it is possible to easily and quickly attach the occluder supporter to the edge of the occluder.

The support is disposed in such a way as to transect the valve opening and to create a condition wherein the contralateral edges of the occluder of the ventricle side of the ventricle valve of a mammalian heart are held in a mutually close position, and the stitched attachments are attached to the aforementioned contralateral edges in order to attach the occluder supporter to the occluder of the atrium side of the ventricle valve. As a result, it is possible to easily and quickly attach the occluder supporter to the edge of the occluder.

The support is disposed so as to create a condition wherein the contralateral edges of the occluder of the atrium side of the ventricle valve of the mammalian heart are held in a mutually close position and so as to transect the valve aperture, and the stitched attachments are attached onto the aforementioned contralateral edges in order to attach the occluder supporter to the occluder of the aortic side of the aortic valve. As a result, it is possible to quickly and easily attach the occluder supporter to the contralateral edges of the occluder of the atrial wall.

BRIEF DESCRIPTIONS OF THE DRAWINGS

DESCRIPTION OF PREFERRED EMBODIMENTS

A explanation of each of the preferred embodiments of the present invention, with reference to the figures, follows below.

First Embodiment

Figure 1:
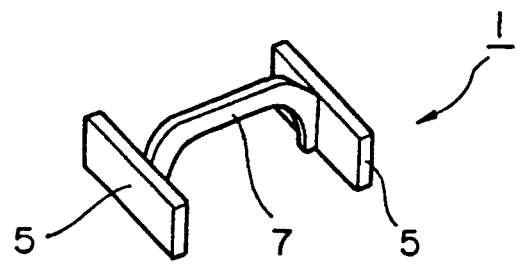
FIG. 1 is a perspective diagram showing the occluder supporter of the first embodiment of the present invention.

FIG. 1 is a perspective view diagram showing occluder supporter 1 of the first embodiment of the present invention.

This occluder supporter is provided to the left atrium side of the bicuspid valve and is a device for preventing valve reflux. Occluder supporter 1 is comprised from stitched attachments 5,5 and support 7.

Figure 2:
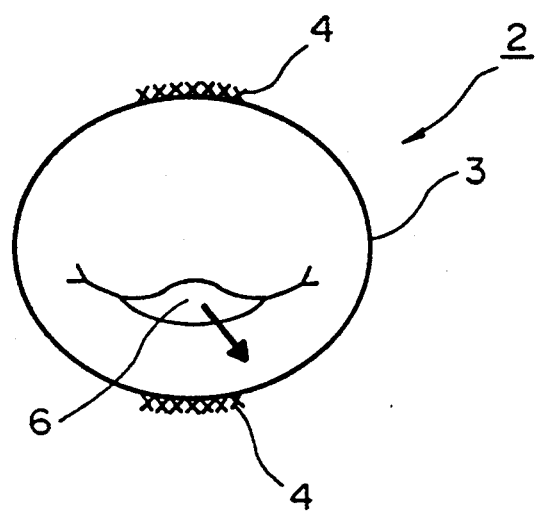
FIG. 2 is a schematic diagram showing the bicuspid valve as seen from the atrial wall of the heart.

Stitched attachments 5,5 are a pair of tabular plate bodies sewed on to contralateral edges 4,4 of occluder 3 of the bicuspid valve 2 shown in FIG. 2. Furthermore, support 7 is provided so as to transect valve aperture 6 in the space between stitched attachments 5,5 and hold and support contralateral edges 4,4 in a mutually close position. Support 7 is a bar having a streamlined cross section and bends in an arc shape.

The base substance of stitched attachments 5,5 and support 7 is comprised from Titanium (Ti), and the surfaces are coated with alumina ($Al_2O_3$), a ceramic which is antithrombotic and antihemolytic. Furthermore, the area of attachment between occluder 3 and stitched attachments 5,5 is covered with poly tetra fluoroethylene, an organic material which is antithrombotic and antihemolytic character.

Furthermore, in addition to Titanium, other noncorrosive metal such as Titanium alloy, stainless steel or the like may be appropriately used as the material for stitched attachments 5,5 and support 7. Additionally, in addition to alumina, other organically appropriate antithrombotic or antihemolytic ceramic such as hydroxyapatite can be used as the ceramic. And, in addition to poly tetra fluoroethylene, other antithrombotic, antihemolytic polyester and the like may be used as the organic material.

Figure 3:
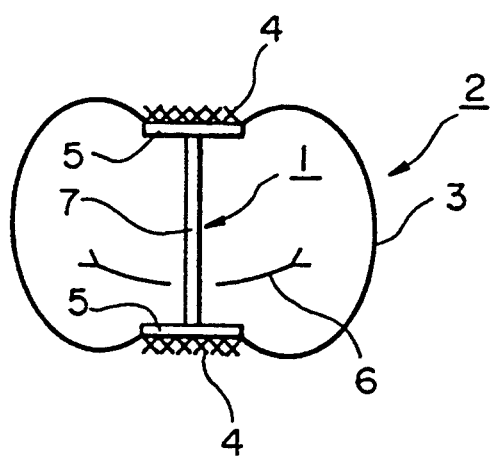
FIG. 3 is a frontal diagram showing the attachment of the occluder supporter of the first embodiment of the present invention to the bicuspid valve which is shown as seen from the atrial side.

As is shown in FIG. 3, in order to attach occluder supporter 1 to occluder 3 of bicuspid valve 2, support 7 is disposed so as to hold contralateral edges 4,4 of occluder 3 in a mutually close position and so as to transect valve aperture 6. Stitched attachments 5,5 are attached to each contralateral edge 4,4.

Because the above occluder supporter 1 has support 7 which connects stitched attachments 5,5 in such a way as to transect the valve aperture 6 for maintaining the edges 4,4 of the occluder 3 so that they are in close proximity to each other, it is possible for the mitrial valve to close completely during the contraction phase of the left ventricle. Accordingly, it is possible to prevent valve reflux.

Because support 7 is a bar which has a streamlined cross section, it is possible to reduce the resistance offered to blood flow. Moreover, because support 7 bends in such a way as to protrude out on the left atrium side, support 7 does not contact with the valve tip.

Because the surfaces of stitched attachments 5,5 and support 7 are covered with an aluminum material having antithrombotic and antihemolytic properties, it is possible to improve the biocompatibility of stitched attachments 5,5 and support 7. Furthermore, it is possible to markedly improve the durability of the occluder supporter without the occluder supporter itself becoming a cause of thrombosis or hemolysis.

In stitched attachments 5,5, because the area of attachment to occluder 3 is covered with poly tetra fluoroethylene, an organic material which is antithrombotic and antihemolytic, it is possible to improve the organic compatibility of stitched attachments 5,5, and to easily carry out the connection of stitched attachments 5,5 to occluder 3.

According to the method for attachment of occluder supporter 1, because support 7 is disposed so as to hold contralateral sides 4,4 of occluder 3 in a close position and so as to transect valve aperture 6, and because stitched attachments 5,5 are attached to each contralateral edge 4,4, occluder supporter 1 can be easily and quickly attached to contralateral edges 4,4 of occluder 3 of the atrium side.

Figure 4:
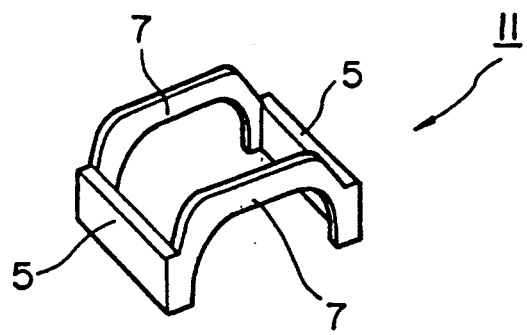
FIG. 4 is a perspective diagram showing a variation of the occluder supporter of the first embodiment of the present invention.

FIG. 4 is a perspective view showing a variation on the embodiment of occluder supporter 1.

In occluder supporter 11, two supports 7,7 are provided in parallel to stitched attachments 5,5.

Figure 5:
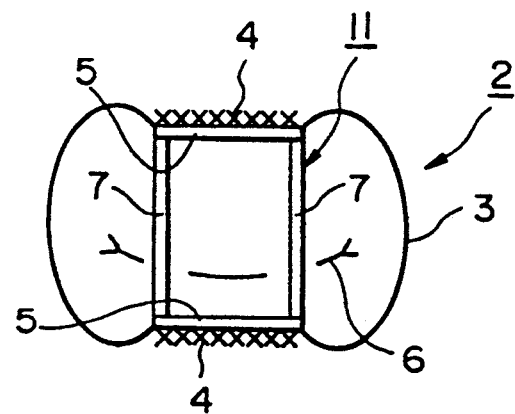
FIG. 5 is a frontal diagram showing the attachment of a variation on the occluder supporter of the first embodiment of the present invention to the bicuspid which is shown as seen from the atrial side.

As shown in FIG. 5, occluder supporter 11 can be attached to occluder 3 of mitrial valve 2 by the same method as employed for occluder supporter 1.

In occluder supporter 11 and in its method of attachment, the same effects and functions are performed as by occluder supporter 1 and in its method of attachment. Additionally, because two supports 7,7 are utilized, it is possible to improve the strength of the device over that of occluder supporter 1.

Second Embodiment

Figure 6:
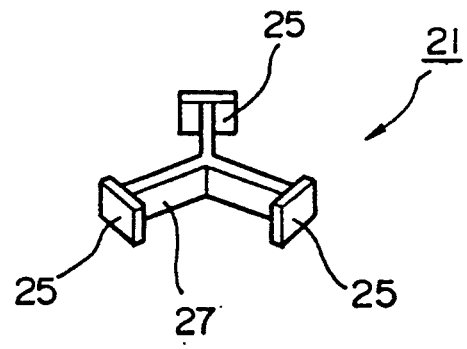
FIG. 6 is a perspective diagram showing the occluder supporter of the second embodiment of the present invention.

FIG. 6 is a perspective view showing occluder supporter 21 of the second embodiment of the present invention. Occluder supporter 21 is a device which is installed to the aortic side of the aortic valve in order to prevent valve reflux. Occluder supporter 21 comprises three stitched attachments 25 and a support 27.

Figure 7:
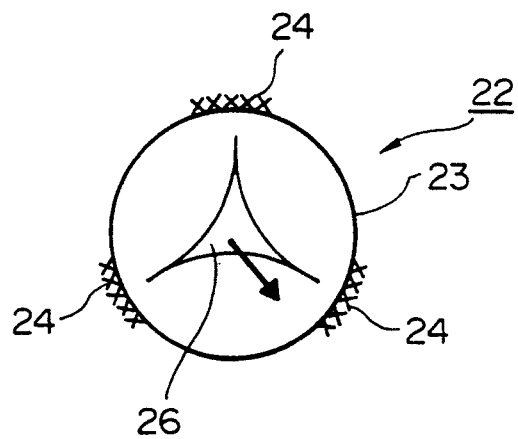
FIG. 7 is a schematic diagram showing the aortic valve as seen from the aortic side of the heart.

Stitched attachments 25 are of a tabular form and are sewn on to each connecting part 24 of occluder 23 of the aortic valve 22 shown in FIG. 7. Furthermore, support 27 is installed between stitched attachments 25 in such a way as to transect valve aperture 26, and is of a tripartite rhabdome shape which supports and holds each connecting part 24 in a close position.

The base substance of stitched attachments 25 and support 27 is formed from Titanium. The surfaces of stitched attachments 25 and support 27 are coated with an antithrombotic, antihemolytic ceramic alumina. The antithrombotic, antihemolytic alumina material covers the surface of stitched attachments 25 and support 27. Additionally, the area of attachment of stitched attachment 25 to occluder 23 is covered by a poly tetra fluoroethylene, an organic material which is antithrombotic and antihemolytic.

In addition to Titanium alloy, other appropriate noncorrosive, antithrombotic, antihemolytic metal, such as stainless steel, may be used as the material for stitched attachments 25 and support 27. Furthermore, in addition to alumina, other biologically compatible, antithrombotic, antihemolytic ceramic, such as hydroxyapatite, may be used as the ceramic. And in addition to poly tetra fluoroethylene, other appropriate antithrombotic, antihemolytic polyester may be used as the organic material.

Figure 8:
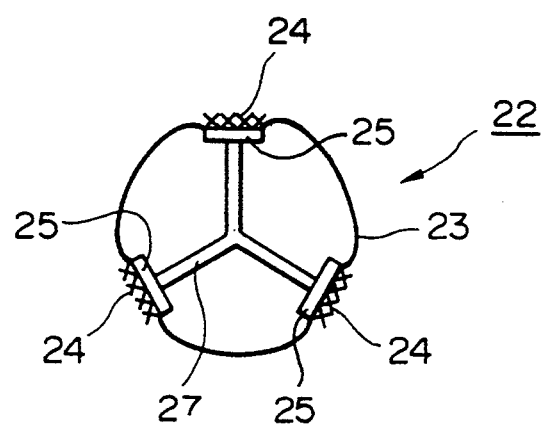
FIG. 8 is a frontal diagram showing the attachment of the occluder supporter of the second embodiment of the present invention to the aortic valve which is shown as seen from the aortic side.

As shown in FIG. 8, support 27 is disposed so as to hold each connecting part 24 of occluder 23 in a mutually close position and so as to transect valve aperture 26, and stitched attachments 25 are sewn on corresponding to each connecting part 24.

Because occluder supporter 21 comprises stitched attachments 25 and support 27 it is possible to create a condition wherein the aortic valve 22 closes completely during the relaxation phase of the left ventricle, accordingly preventing valve reflux.

Because support 27 is a tripartite bar having a streamlined cross section, it is possible to improve the strength of support 27 while at the same time reduce the resistance offered with respect to blood flow.

Because the surfaces of stitched attachments 25 and support 27 are covered with an antithrombotic, antihemolytic alumina, it is possible to improve biologic compatibility thus ensuring that occluder supporter 21 itself does not become a cause of thrombosis or hemolysis, and to markedly improve the durability of stitched attachments 25 and support 27.

In stitched attachments 25, because the area of attachment to occluder 23 is covered with a poly tetra fluoroethylene, an antithrombotic, antihemolytic organic material, it is possible to improve the biological compatibility of stitched attachments 25 and to easily carry out the attachment of stitched attachments 25 to occluder 23.

According to the method of attachment of occluder supporter 21, support 27 is disposed so as to hold each connecting part 24 of occluder 23 in a mutually close position and so as to transect valve aperture 26, with stitched attachments 25 being attached corresponding to these connecting parts 24. For this reason, it is possible to easily and quickly attach occluder supporter 21 to each connecting part 24 of occluder 23.

Figure 9:
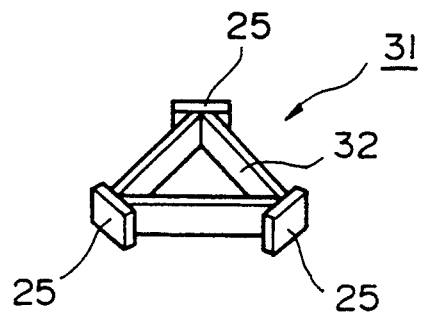
FIG. 9 is a perspective view showing a variation of the occluder supporter of the second embodiment of the present invention.

FIG. 9 is a perspective diagram showing a variation on the preferred embodiment of occluder supporter 21.

Occluder 31 is formed from the provision of a triangular streamlined shaped support 32 in the space between stitched attachments 25, and from the fixing of the top section of support 32 to each stitched attachment 25.

Figure 10:
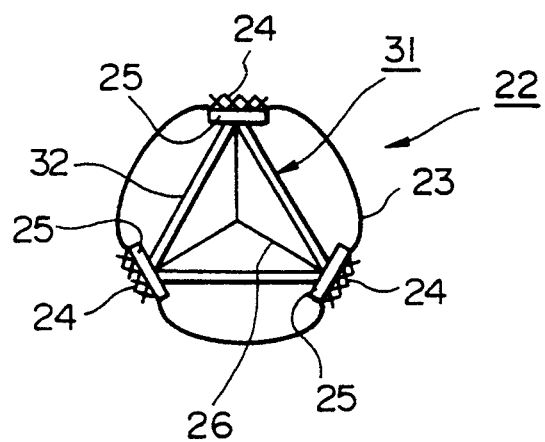
FIG. 10 is a frontal diagram showing the attachment of a variation on the occluder supporter of the second embodiment of the present invention to the aortic valve which is shown as seen from the aortic side.

As shown is FIG. 10, occluder supporter 31 can be attached to occluder 23 of the aortic valve by the same method as employed for occluder supporter 21.

In occluder supporter 31 and in its method of attachment, the same effects and functions can be performed as by occluder supporter 21 and in its method of attachment. Furthermore, because support 32 is a triangular shaped support having a streamlined cross section it is possible to improve the strength of support 32 while at the same time to decrease the resistance offered to blood flow.

What is claimed is:

1. On a heart valve of a mammalian heart having an atrium and a ventricle connected to an artery, the heart valve having an annular occluder with edges connected to the heart and a plurality of valve cusps extending inwardly from said edges for forming the outer circumference of a valve aperture, the valve aperture being opened and shut by the cusps and permitting blood flow in one direction and preventing back flow of blood; an occluder supporter comprising:
   a plurality of stitched attachments shaped and configured to be sewn on to said edges of said annular occluder at angularly spaced positions, and
   support means connecting said stitched attachments for maintaining said edges of said annular occluder in close proximity to each other and facilitating closure of said cusps in such a way that said support means transect the valve aperture.

2. An occluder supporter according to claim 1 shaped and configured to be mounted on the atrium side of a ventricle valve and said support means being bent in such a way as to protrude out into the atrium side.

3. An occluder supporter according to claim 1 shaped and configured to be mounted on said artery side of an arterial valve, said support means being bent into such a way as to protrude out into the artery side.

4. An occluder supporter according to one of claims 2 or 3, wherein said support means comprises a bar.

5. An occluder supporter according to claim 2, wherein said support means comprises a plurality of parallel bars provided in a space between said stitched attachments.

6. An occluder supporter according to claim 3, wherein said support means has a tripartite shape having three edges radiating in three directions, and said stitched attachments being respectively fixed to each edge of said support.

7. An occluder supporter according to claim 3, wherein said support means has a triangular shape having three apexes, and said stitched attachments being respectively fixed to each apex of said support.

8. An occluder supporter according to one of claims 2 or 3, wherein said stitched attachments have a width wider than that of said support means.

9. An occluder supporter according to one of claims 2 or 3, wherein said occluder supporter is comprised of an antithrombotic and antihemolytic material.

10. An occluder supporter according to one of claims 2 or 3, wherein said occluder supporter is covered by an antithrombotic and antihemolytic material.

11. An occluder supporter according the claim 10, wherein a principal component of said antithrombotic and antihemolytic material is a ceramic material.

12. An occluder supporter according to one of claims 2 or 3, wherein said stitched attachments are covered by an antithrombotic and antihemolytic organic material.

13. An occluder supporter according to claim 12, wherein a principal component of said organic material is one of poly tetra fluoroethylene and polyester.

* * * * *